United States Patent [19]

Collier et al.

[11] Patent Number: 4,709,017

[45] Date of Patent: Nov. 24, 1987

[54] MODIFIED TOXIC VACCINES

[75] Inventors: R. John Collier, Wellesley Hills; Stephen F. Carroll, Brookline, both of Mass.

[73] Assignee: President and Fellows of Harvard College, Cambridge, Mass.

[21] Appl. No.: 742,618

[22] Filed: Jun. 7, 1985

[51] Int. Cl.$^4$ ............................................. C07K 13/00
[52] U.S. Cl. ..................................................... 530/350
[58] Field of Search ........................... 514/12; 530/350

[56] References Cited

U.S. PATENT DOCUMENTS 4,554,101 11/1985 Hopp ...................................... 514/12

OTHER PUBLICATIONS

Biological Abstract, vol. 63, (1977) 52070.
Biological Abstract, vol. 62, (1976) 50839.
Biological Abstract, vol. 73, (1982) 3631.
Biological Abstract, vol. 76 (1983) 69140.
Biological Abstract, vol. 77, (1984) 3975.
Biological Abstract, vol. 78, (1984) 43662.
Chem. Abstr., vol. 83, (1975) 23227.
The Journal of Biological Chem., vol. 254, (1979) 5838-5842.
Emerick et al., DNA, 4(1): 78 (1985).
Collier in The Specificity of Action of Animal, Bacterial, and Plant Toxins, Cuatrecasas ed., Chapman & Hall, London, 1976, pp. 69-98.
Alouf, Toxicon (1982), vol. 20, pp. 211-216.
Carroll et al., J. Biological Chemistry (1980), vol. 225, pp. 12,020-12,024.
Michel and Dirkx, Biochem. Biophys. Acta (1977), vol. 491, pp. 286-295.
Uchida et al., J. Biol. Chem., vol. 248, pp. 3838-3844.
Carroll and Collier, Proc. Nat'l Acad. Sci., (1984), vol. 81, pp. 3307-3311.

Primary Examiner—Delbert R. Phillips

[57] ABSTRACT

Diphtheria toxin, fragment A, which has been modified by the deletion of Glu-148 or the substitutions of Glu-148 with Asp is catalytically inactive and immunologically cross-reactive with naturally occurring diphtheria toxin, fragment A. The modified diphtheria toxin is compounded with a pharmacologically suitable vehicle to form a vaccine that is innoculated into a mammal to generate immunological protection against diphtheria toxin. The modified diphtheria toxin is produced by a cell that includes a vector having DNA encoding the non-toxic protein and regulatory DNA capable of effecting its expression.

2 Claims, 1 Drawing Figure

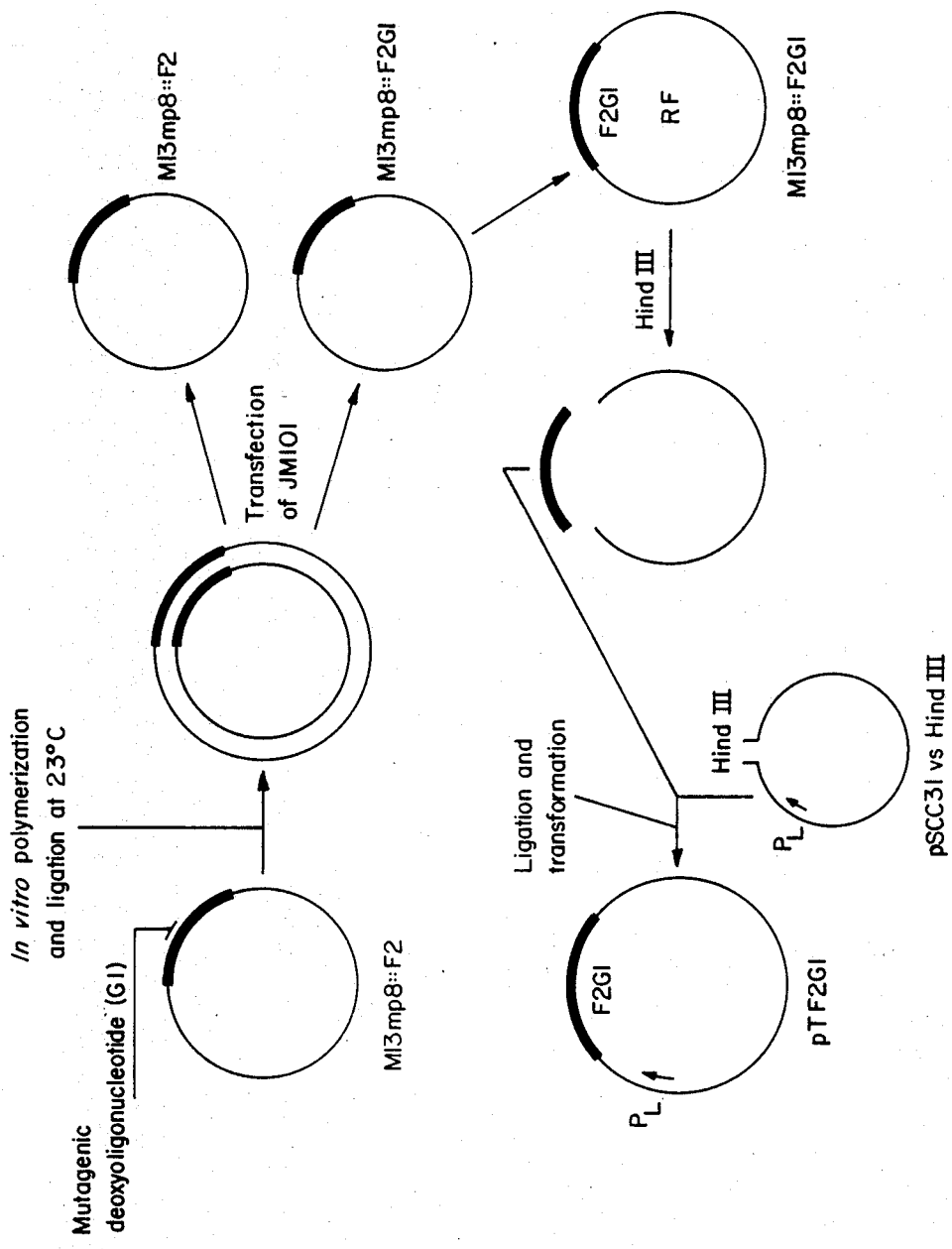

MODIFIED TOXIC VACCINES

BACKGROUND OF THE INVENTION

The invention described in this application was made at least in part during work funded by the following grants: Public Health Service Grant AI-07877 from the National Institute of Allergy and Infections Diseases; and Grant CA-30663 from the National Cancer Institute. The U.S. Government has rights in this invention.

This invention relates to modifying bacterial toxins that transfer an ADP-ribose unit from NAD to a target protein of the infected cell and to protecting against such toxins.

Certain bacterial toxins, with we will refer to as ADP-ribose-transfer toxins ("ART toxins"), are known to operate by severing the ADP-ribose unit from NAD and transferring that unit to a target protein of the affected cell, thereby inactivating the protein. For example, diphtheria toxin and exotoxin A of *Pseudomonas aeruginosa* transfer ADP-ribose to elongation factor 2 (EF-2), a factor essential for protein synthesis (Collier in the *The Specificity of Action of Animal, Bacterial, and Plant Toxins*, Cuatrecasas ed., Chapman & Hall, London 1976, p. 69). Cholera toxin (i.e. toxin produced by members of the species *Vibrio cholerae*) and other toxins, such as those produced by *Bordetella pertussis* and *Escherichia coli*, operated by transfer of ADP-ribose to subunits of the adenylate cyclase system (Alouf, *Toxicon* (1982) 20: 211–216).

Various studies of the structure and mechanism of ART toxins are reported in the prior art.

Carroll et al., *J. Biological Chemistry* (1980) 225: 12,020–12,024 disclose photoinduced ($\lambda = 253.7$ nm) cross-linkage of ATP or NAD with the complete diphtheria toxin molecule, consisting of an A subunit and a B subunit linked by a disulfide bridge. The NAD/ATP site is reported to be on the A subunit and to be same as the site at which NAD binds to the A subunit in the absence of subunit B. No conclusion was drawn as to whether both ligands bind to the same site on the A fragment.

Michel and Dirkx, *Biochem. Biophys. Acta* (1977) 491: 286–295 disclose that chemical modification of the Trp-153 amino acid of the diphtheria toxin subunit A blocks catalysis by the subunit of the hydrolysis of the NAD-glycolytic bond and of the transfer of ADP-ribose.

Formalin treatment has been used to stabilize and to modify the diphtheria toxin making it non-toxic, while retaining antigenicity that protects against the natural toxin. However, the use of such modified toxins as a vaccine against diphtheria toxin poses the risk of reversion to the active, toxic form.

Mutants of the species *Corynebacterium diphtheriae* have been generated that produce enzymatically inactive proteins corresponding sufficiently to the natural toxin to produce an immune response that protects against the natural toxin. For example, the toxin designated CRM-197 referenced in Uchida et al. J. Biol. Chem. 248: 3838–3844 is such an inactive toxin.

SUMMARY OF THE INVENTION

Diphtheria toxin, fragment A, which has been modified by the deletion of Glu-148 or the substitution of Glu-148 with Asp, is catalytically inactive and immunologically cross-reactive with naturally occurring diphtheria toxin, fragment A. Catalytically inactive means that the modified toxin's ADP-ribose-transferring activity is not detectable, or is insignificant; immunologically cross-reactive means the modified toxin (or a conjugate containing the modified toxin) raises an antibody that substantially reacts with diphtheria toxin.

The CIIC protein is compounded with a pharmacologically suitable vehicle to form a vaccine that is innoculated into a mammal to generate immunological protection against diphtheria-toxin. The modified toxin is produced by culturing a cell that includes a DNA vehicle having DNA encoding the modified toxin and regulatory DNA capable of effecting its expression.

The invention provides reliable, safe protection using a non-toxic molecule to generate an immune response that protects against the natural diphtheria toxin, yet is reliably modified to minimize or eliminate entirely catalysis of the toxic ADP-ribose-transfer.

DESCRIPTION OF THE PREFERRED EMBODIMENT

We first briefly describe the drawing.

Drawing

FIG. 1 is a diagram of the construction of a vector containing a segment coding for modified diphtheria toxin.

PRODUCING THE NON-TOXIC PROTEIN

Modified diphtheria toxin is prepared by genetically engineering the natural structural gene, e.g. of the diphtheria toxin fragment A. The naturally occurring structural gene can be obtained, e.g. by cloning from the DNA of Beta phage of *C. diphtheriae* such as ATCC 11952. The structural gene is spliced in a suitable cloning vector and modified by site-directed mutagenesis as described below.

A specific method of preparing a gene coding for a modified diphtheria toxin involves the use of Beta phage DNA from a *C. diphtheriae* bacterium such as the one described above. The Beta phage DNA is digested with MspI, and a segment, identified with an oligodeoxynucleotide probe such as the 18-base probe described below, is separated and cloned into pBR322 to yield pRTF2 as described generally in Tweten and Collier (1983) J. Bacteriol. 156: 680–685. The F2 diphtheria toxin gene encodes a fusion protein containing the entire A fragment of diphtheria toxin and 189 residues of the B fragment. The F2 fragment is subcloned from pRTF2 into the HindIII site of M13mp8 (New England Biolabs, Beverly, MA) and subjected to oligodeoxynucleotide directed mutagenesis as described by Miyada et al., cited above, with two modifications. The 18-base oligodeoxynucleotide (5'-dTCGCGTGTAGTGCTCAGC), which anneals 30 bases upstream of the site of mutagenesis, is included to increase the efficiency of polymerization (Messing, *Methods in Enzymology* (1983) 101C: 20–78), and the polymerization reaction is performed at 23° C., which increases the number of transfectants. A 13-base oligodeoxynucleotide (5'-dCGTTGA̲TTATT; abbreviated G1) containing a single base change (underlined), relative to the wild-type sequence, is used to change the GAA codon at amino acid position 148 to GAT, thereby converting glu at this position to asp. In vitro mutagenized M13mp8::F2 is transformed into JM101 (New England Biolabs) by the general technique described in Maniatis et al. (1982) Molecular Cloning—A Laboratory Manual, Cold Spring Harbor Laboratory, CSH, N.Y. Isolated plaques are picked to fresh agar. Phage-infected colonies are lysed onto nitrocellulose filters. The DNA is fixed to the filter and hybridized by the general method of Miyada, J. Bacteriol. 156: 680–685 (1983), with $^{32}$P-oligodeoxynucleotide containing the desired base change. Filters are washed free of unbound probe and incubated at successively higher temperatures to discriminate between phage carrying the wild-type DNA sequence and those carrying the desired base change. The mutation is confirmed by DNA sequencing by the general method of Sanger et al. J. Mol. Biol. (1982) J. Mol. Biol. 162: 729–773, using the 18-base oligodeoxynucleotide (5'-dTCGCGTGTAGTGCT-CAGC) sequencing primer. Plasmid and M13mp8 restriction fragments are prepared as described by Birnboim and Doly, Nucleic Acid Res. (1979) 7: 1513–1523, and single-stranded M13mp8 DNA is isolated according to the method of Hines and Ray, Gene (1980) 11: 207–218, after a 6–7 hour propagation of phage.

To express the modified fragment, the HindIII fragment from the altered F2 (asp-148) gene fragment is subcloned into an appropriate vector, for example, pBR322, and transformed into a strain of E. coli such as PK1022 or JM101 (New England Biolabs) by the general technique of Tweten and Collier, cited above. Transformants are grown overnight at 32° C. in L-broth, diluted 1:50 into fresh medium, and grown for 90 minutes at 32° C. The temperature is shifted to 42° C., and after 4 hours, cells are harvested and the periplasmic fraction is isolated as described by Tweten and Collier, cited above. The periplasmic fraction is desalted by gel filtration over Sephadex-50 equilibrated in 50 mM Tris-HCl, pH 7.4, containing 1 mM EDTA, and the peptides produced by the clone are quantified by radioimmunoassay. Immunoblot analysis and measurement of ADP-ribosyltransferase activity are performed as previously described in Tweten and Collier, cited above.

ADP-ribosylation activity can be measured eluting the modified toxin protein from a SDS polyacrylamide gel, slicing a lane into 6 mm fractions, and eluting each slice into 0.5 ml 50 mM Tris-HCl, pH 7.4, 0.1 mg ovalbumin per ml, overnight at 4° C. Ten μl of the eluate is assayed for ADP-ribosylation activity using the following assay mixture: 50 mM Tris pH 8.2, 1 mM EDTA, 40 mM dithiothreitol, 10 nM $^{32}$P-NAD (specific activity=250 Ci per mmole), wheat germ EF-2, and periplasmic fraction in a final vol of 100 μl. After 2 hours at 37° C., trichloroacetic acid precipitable material was determined as described by Tweten and Collier, cited above.

Fragment A containing aspartic acid at position 148 has no significant ADP-ribosylation activity; for example, it has less than 0.6% the ADP-ribosylation activity of wild-type fragment A. The mutation produces no change in sensitivity of fragment A to trypsin and little, if any, reduction in affinity of fragment A for NAD.

These results indicate that glutamic acid-148 is essential for the ADP-ribosylation of elongation factor 2.

Thus, when glu-148 of the diphtheria toxin fragment A is replaced with asp, the resulting protein is a suitable immunogenic component of a vaccine that protects against diphtheria toxin. Specifically, the modified toxin is generally catalytically inactive and non-toxic. However, its structural similarity to the natural toxin is sufficient to raise antibodies that cross-react with the natural toxin with high specificity.

The end-product of the procedure diagrammed in FIG. 1 is pTF2G1, which has been deposited in E. coli with the American Type Culture Collection in Rockville, MD under ATCC No. 11952. Applicant's assignee acknowledges its responsibility to replace this deposit should the deposit become non-viable before the end of the term of a patent issued hereon, and its responsibility to notify the ATCC of the issuance of such a patent, at which time the deposits will be made available to the public. Until that time the deposits will be made available to the Commissioner of Patents under the terms of 37 CFR §1.14 and 35 USC §112.

The plasmid pTF2G1 contains genetic elements capable of expressing the non-toxic protein identical to the diphtheria toxin A chain, with the substitution of asp for glu at position 148. Expression can be enhanced by adding to pTF2G1 known suitable regulatory elements for improved transcription and translation of that structural gene in E. coli.

The non-toxic protein can be produced by standard techniques of culturing E. coli, allowing expression of the structural gene, and recovering the protein. Non-toxicity of the protein is established by enzymatic tests for ADP-ribosylating activity described above as well as by standard in vivo toxicological techniques. The protein's ability to raise antibodies that cross-react with the natural toxin can be demonstrated by standard immunological procedures such as flocullation tests or competitive radioimmunoassay, or by animal immunization studies. Similarly, effective vaccination regimes can be established by such tests.

OTHER EMBODIMENTS

Other embodiments are within the following claims. The above-described cloning procedures may be used to delete glu-148 from diphtheria toxin fragment A. Emerick et al., DNA (1985) 4: 78, describe such a modified toxin. The modified toxin is useful for evaluating the cell-selectivity and delivery of toxins or immunotoxins, without killing the cells.

What is claimed is:

1. Diphtheria toxin, fragment A, modified by the deletion of Glu-148 or by the substitution of Asp for Glu-148.

2. The modified diphtheria toxin of claim 1 in a mixture comprising a pharmaceutically acceptable carrier.

* * * * *

UNITED STATES PATENT AND TRADEMARK OFFICE
CERTIFICATE OF CORRECTION

PATENT NO. : 4,709,017
DATED : November 24, 1987
INVENTOR(S) : R. John Collier et al.

It is certified that error appears in the above-identified patent and that said Letters Patent are hereby corrected as shown below:

Col. 1, line 8, "Infections Diseases" should be --Infectious Diseases--.

Col. 1, line 15, "with we will refer to as" should be --which we will refer to as--.

Col. 4, line 14, "ATCC No. 11952" should be --ATCC No. 53144--.

Col. 4, line 38, "flocullation" should be --flocculation--.

Signed and Sealed this

Nineteenth Day of April, 1988

Attest:

DONALD J. QUIGG

*Attesting Officer*   *Commissioner of Patents and Trademarks*